US012708756B2

(12) United States Patent
Nix et al.

(10) Patent No.: US 12,708,756 B2
(45) Date of Patent: Aug. 18, 2026

(54) SYSTEM AND METHOD FOR VENTRICULAR ASSISTANCE SUPPORT DURING EXTRACORPOREAL MEMBRANE OXYGENATION

(71) Applicant: Abiomed Europe GmbH, Aachen (DE)

(72) Inventors: Christoph Nix, Aachen (DE); Stefan Boensch, Aachen (DE); Katrin Lunze, Aachen (DE)

(73) Assignee: ABIOMED EUROPE GmbH, Aachen (DE)

( * ) Notice: Subject to any disclaimer, the term of this patent is extended or adjusted under 35 U.S.C. 154(b) by 752 days.

(21) Appl. No.: 17/939,335

(22) Filed: Sep. 7, 2022

(65) Prior Publication Data

US 2023/0083542 A1 Mar. 16, 2023

Related U.S. Application Data

(60) Provisional application No. 63/257,715, filed on Oct. 20, 2021, provisional application No. 63/242,828, filed on Sep. 10, 2021.

(51) Int. Cl.

| | |
|---|---|
| ***A61M 60/546*** | (2021.01) |
| ***A61M 60/13*** | (2021.01) |
| ***A61M 60/174*** | (2021.01) |
| ***A61M 60/216*** | (2021.01) |
| ***A61M 60/414*** | (2021.01) |
| ***A61M 60/508*** | (2021.01) |

(52) U.S. Cl.

CPC .......... *A61M 60/13* (2021.01); *A61M 60/174* (2021.01); *A61M 60/216* (2021.01); *A61M 60/414* (2021.01); *A61M 60/508* (2021.01)

(58) Field of Classification Search

CPC .............. A61M 60/531; A61M 60/546; A61M 2205/3334; A61M 2205/3365

See application file for complete search history.

(56) References Cited

U.S. PATENT DOCUMENTS

| | | | | |
|---|---|---|---|---|
| 8,870,552 | B2 | 10/2014 | Ayre et al. | |
| 10,960,118 | B2 | 3/2021 | Sunagawa | |
| 2001/0002234 | A1 | 5/2001 | Woodward et al. | |
| 2003/0091450 | A1 | 5/2003 | Davis et al. | |
| 2005/0159639 | A1 * | 7/2005 | Skliar ................ | A61M 60/178 600/16 |
| 2016/0245669 | A1 | 8/2016 | Nomura | |
| 2018/0280601 | A1 | 10/2018 | Harjes | |
| 2020/0018318 | A1 | 1/2020 | Chen | |
| 2020/0038569 | A1 | 2/2020 | Sunagawa | |

OTHER PUBLICATIONS

International Search Report and Written Opinion for corresponding PCT Application No. PCT/US22/23486, dated Sep. 22, 2022.

EESR corresponding to EP App. No. 25220317.9, issued Feb. 19, 2026.

* cited by examiner

*Primary Examiner* — Michael J D'Abreu

(74) *Attorney, Agent, or Firm* — Meagher Emanuel Laks Goldberg & Liao, LLP

(57) ABSTRACT

A controller for a blood pump, in particular a catheter-based intravascular blood pump, configured to utilize detected or determined aortic pressures and left ventricular pressures in order to calculate a coupling factor, which is then used to determine how to adjust the rotational speed of the blood pump, such as when the blood pump is used in conjunction with ECMO devices.

25 Claims, 10 Drawing Sheets

SYSTEM AND METHOD FOR VENTRICULAR ASSISTANCE SUPPORT DURING EXTRACORPOREAL MEMBRANE OXYGENATION

CROSS-REFERENCE TO RELATED APPLICATIONS

The present application claims priority to U.S. Provisional Patent Application Nos. 63/242,828, filed Sep. 10, 2021, and 63/257,715, filed Oct. 20, 2021, the contents of which are incorporated by reference herein in their entirety.

TECHNICAL FIELD

The disclosed embodiments relate to a control system for extracorporeal membrane oxygenation.

BACKGROUND

Cardiogenic shock is the leading cause of death for patients with acute myocardial infarction (AMI) who reach the hospital alive. Cardiogenic shock is caused by a heart malfunction or problem, which leads to an inability of the heart to eject enough blood for the body. Cardiogenic shock is sometimes referred to as obstructive shock.

Extracorporeal Membrane Oxygenation (ECMO) and Extra-Corporeal Life Support (ECLS) allow for gas exchange of the blood when the lungs do not work properly. For example, Veno-Arterial Extracorporeal Membrane Oxygenation (VA-ECMO) and Veno-Venous Arterial Extracorporeal Membrane Oxygenation (VVA-ECMO) may involve the use of a mechanical circulatory device for patients experiencing oxygenation issues (e.g., for lung support). In some instances, ECMO may be used for patients experiencing oxygenation issues due to cardiogenic shock, or other forms of hemodynamic deterioration. In such instances, the use of such devices may result in an increase in left ventricular afterload.

Ventricular assist devices (VADs) and catheter-based ventricular assist devices (such as intravascular blood pumps) may be used to mechanically unload the left ventricle (e.g., reducing the left ventricular volume, which results in pressure reduction) and/or decompression of the left ventricle (e.g., volume reduction of the left ventricle, which may be drive by a hole in the wall between the left atrium and right atrium resulting in a lower preload of the left ventricle). In some instances, such independent support flow may be insufficient for independently treating cardiogenic shock.

BRIEF SUMMARY

According to a first aspect of the present disclosure, a controller for a blood pump, such as an intravascular blood pump, includes a processor configured to control a rotational speed of a motor of a catheter-based intravascular blood pump using a first selectable operating mode. The first selectable operating mode includes the following steps: determining a coupling factor k using a detected or determined aortic pressure value and a detected or determined left ventricular pressure value and adjusting the rotational speed of the motor based on the determined value of the coupling factor k. Broadly, the first selectable operating mode may case at least one adjustment to the rotational speed of the motor based on the determined value of the coupling factor k, the at least one adjustment being: increasing the rotational speed of the motor by a first amount when the coupling factor k is greater than a first threshold value; increasing the rotational speed of the motor by a second amount when the coupling factor k is less than or equal to the first threshold value and greater than a third threshold value, the second amount being smaller than the first amount; decreasing the rotational speed of the motor by a third amount when the coupling factor k is greater than or equal to a fourth threshold value and less than a second threshold value; decreasing the rotational speed of the motor by a fourth amount when the coupling factor k is greater than or equal to a fifth threshold value and less than the fourth threshold value, the fourth amount being larger than the third amount; decreasing the rotational speed of the motor by a fifth amount when the coupling factor k is less than a fifth threshold value, the fifth amount being larger than the fourth amount; or a combination thereof. Optionally, the first selectable operating mode may be further configured to keeping the rotational speed of the motor constant when the coupling factor is equal to the second threshold value.

In some embodiments, in the first selectable operating mode, the controller is configured such that when the coupling factor is outside of a target range of values, the controller will attempt to bring the coupling factor back to a target value, then will not make any additional adjustments until the coupling factor is outside the target range. The controller only starts a speed adjustment process when the coupling factor k is greater than a first threshold value or less than a second threshold value. In particular, the speed is adjusted as follows:

When it is determined that the coupling factor k is greater than the first threshold value, the controller begins a subroutine where it increases the rotational speed of the motor in steps until the coupling factor k is below a predetermined value. In particular during the subroutine, the rotational speed of the motor is increased by a first amount when the coupling factor k is greater than the first threshold value and increased by a second amount when the coupling factor k is less than or equal to the first threshold value but above a third threshold value, after which the pressures are measured, and a coupling factor is determined. This cycle repeats until the coupling factor k is determined to be less than or equal to the third threshold value, at which point it exits this subroutine and returns to monitoring the coupling factor and only adjusting when the coupling factor is greater than the first threshold value or less than the second threshold value.

When it is determined that the coupling factor k is less than the second threshold value, the controller begins a subroutine where it decreases the rotational speed of the motor in steps until the coupling factor k is above a predetermined value. In particular during the subroutine, the rotational speed of the motor is decreased by a third amount when the coupling factor k is greater than or equal to the second threshold value and less than the fourth threshold value; decreased by a fourth amount when the coupling factor k is greater than or equal to the fifth threshold value and less than the second threshold value, the fourth amount being greater than the third amount; and/or decreased by a fifth amount when the coupling factor k is less than a fifth threshold value, after which the pressures are measured, and a coupling factor is determined. This cycle repeats until the coupling factor k is determined to be less than or equal to the third threshold value, at which point it exits this subroutine and returns to monitoring the coupling factor and only adjusting when the coupling factor is greater than the first threshold value or less than the second threshold value.

The processor may be configured to adjust the rotational speed of the motor in the first selectable operating mode within a first predetermined time interval t (which may be, e.g., between every 5 and 20 seconds, such as 10 seconds).

In some embodiments, the coupling factor k is determined in a second predetermined time interval (which may be, e.g., between every 1 and 5 seconds, such as 2 seconds).

In some embodiments, the coupling factor k is a quotient of an average of the detected or determined left ventricular pressure value and of an average of the detected or determined aortic pressure value.

In some embodiments, the average of the detected or determined left ventricular pressure value and the average of the detected or determined aortic pressure value is determined over a third predetermined time interval (which may be, e.g., between 8 and 12 seconds, such as 10 seconds).

In some embodiments, the first threshold value is 0.75, the second threshold value is 0.55, the third threshold value is 0.65, the fourth threshold value is 0.65, and the fifth threshold value is 0.15.

In some embodiments, the first threshold value is a target coupling factor k value plus a defined value, the second threshold value is the target coupling factor k value minus the defined value, the third target coupling factor k and the fourth target coupling factor k are the target coupling factor k value, and the fifth threshold value is a value that is 15%-35% of the target coupling factor k value.

In some embodiments, when the speed of the motor is adjusted by different amounts, the second amount and the third amount are 0.8-1.9% of an operating range (which may be, e.g., between 12,000 rpm and 22,000 rpm, determined as the difference between the maximum operating speed and minimum operating speed that the processor is configured to provide control within) of the rotational speed of the motor within which the processor is configured to perform the first selectable operating mode, the first amount and fourth amount are 2-4.5% of the operating range, and the fifth amount is 8-19% of the operating range.

In some embodiments, the processor is further configured to detect suction events, and respond to such suction events by: causing the rotational speed of the motor to decrease by a fifth amount if a first suction event is detected, causing the rotational speed of the motor to decrease by a sixth amount if a second suction event is detected, and reducing an upper limit of the rotational speed of the motor by the sixth amount for a first period of time (such as, e.g., between 10 minutes and 30 minutes, or 20 minutes) after the second suction event is detected within a predetermined window of time (such as between 30 seconds and 5 minutes, or 2 minutes).

The processor also may be configured to: detect whether an ECMO device (such as an VVA-ECMO or VA-ECMO) is operably connected to the controller and prevent the selection or performance of the first selectable operating mode if the VA-ECMO device is not detected; receive a selection indicating the processor should operate the blood pump using the first selectable operating mode; or a combination thereof. In some embodiments, the processor may be configured to receive input indicating a user confirms an ECMO device has been connected.

In some embodiments, a startup process is used that quickly and safely gets the pump up to an appropriate operating speed. To accomplish this, the processor may be configured to, prior to performing the first selectable operating mode: increase the rotational speed of the motor from zero to a minimum rotational speed the processor is configured to use when performing the first selectable operating mode (such as between 5,000 rpm and 50,000 rpm, or between 20,000 rpm and 40,000 rpm, and/or between 25,000 and 31,000 rpm); determine the coupling factor k using a detected or determined aortic pressure value and a detected or determined left ventricular pressure value; and adjust the rotational speed of the motor based on the value of the coupling factor k. In particular, the speed is adjusted by: if $k \geq 1$, increasing the rotational speed by a sixth amount, and after a fixed period of time (such as, e.g., between 5 and 30 seconds, or 10 seconds), repeating the determining and adjusting steps; and if $k<1$, adjusting the rotational speed of the motor according to the first selectable operating mode, and after the fixed period of time, control the rotational speed of the motor according to the first selectable operating mode.

In some embodiments, the sixth amount is between 5% and 30% of a range of the rotational speed of the motor within which the processor is configured to perform the first selectable operating mode.

The controller also may be configured to allow the motor to operate in other modes, such as when the blood pump is not operating in parallel with an ECMO device. In some embodiments, the processor may be configured to operate in a second selectable operating mode where the processor receives a selection of one of a plurality of predetermined operating rotational speeds and adjusts the speed of the motor to the selected predetermined operating rotational speed; and a third selectable operating mode where the processor is configured to increase the rotational speed of the motor at a predetermined rate to a maximum operating rotational speed.

In some embodiments, the controller is configured to exit the first selectable operating mode if the pressure values used to control the motor are determined to be unreliable. In some embodiments, while operating using the first selectable operating mode, the processor is further configured to determine if the detected or determined aortic pressure value, the detected or determined left ventricular pressure value, or both are unreliable, and when the detected or determined aortic pressure value, the detected or determined left ventricular pressure value, or both have been determined as unreliable for a second period of time (such as, e.g., between 30 seconds and 5 minutes, or between 1 minutes and 3 minutes, or 2 minutes), switch from the first selectable operating mode to the second selectable operating mode.

The processor also may be configured to cause an alarm notification to be activated if the coupling factor k is determined to be less than the fifth threshold value until the coupling factor k is determined to be greater than or equal to a sixth threshold value, the sixth threshold value being greater than the fifth threshold value and less than the fourth threshold value. In some embodiments, the sixth threshold value is between 20% and 15% of a target coupling factor k value.

In some embodiments, the controller further comprises a display controlled by the processor, a first port configured to operably connect the processor with the catheter-based intravascular blood pump, an additional port configured to operably connect the processor with an extra-corporeal membrane oxygenation (ECMO) system; and a housing configured to contain at least the processor.

According to a second aspect of the present disclosure, a blood pump system includes a blood pump controller as described above, and a catheter-based intravascular blood pump operably connected to the blood pump controller.

According to a third aspect of the present disclosure, a system for Extracorporeal Membrane Oxygenation (ECMO) with Ventricular Assistance includes an extra-corporeal membrane oxygenation (ECMO) system, and a blood pump system adapted to work in parallel with the ECMO system, the blood pump system includes a controller as described above and a catheter-based intravascular blood pump operably connected to the controller.

According to a fourth aspect of the present disclosure, a method for starting a blood pump, such as a catheter-based intravascular blood pump when used in coordination with an ECMO system. The method generally includes: increasing a rotational speed of a motor of a catheter-based intravascular blood pump from zero to a predetermined minimum rotational speed (such as, e.g., between 5,000 rpm and 50,000 rpm, or between 20,000 rpm and 40,000 rpm, or 31,000 rpm); and determining a coupling factor k using a detected or determined aortic pressure value and a detected or determined left ventricular pressure value, and if $k \geq 1$, increasing the speed by a fixed amount (such as, e.g., between 5% and 30% of an operating range), and after a fixed period of time, repeating the steps of measuring pressures and determining a coupling factor k until $k<1$.

In some embodiments, after the coupling factor k is determined to be less than 1, automatically switching to an automatic speed control mode adapted for use in coordination with an extra-corporeal membrane oxygenation (ECMO) system.

A fifth aspect of the present disclosure is a method for operating a blood pump, such as a catheter-based intravascular blood pump when used in coordination with an extra-corporeal membrane oxygenation (ECMO) system. The method generally includes: determining a coupling factor k using a detected or determined aortic placement value and a detected or determined left ventricular placement value; and adjusting a rotational speed of a motor of a catheter-based intravascular blood pump based on the determined value of the coupling factor k.

The method involves making at least one adjustment to the rotational speed of the motor based on the determined value of the coupling factor k, the at least one adjustment being: increasing the rotational speed of the motor by a first amount when the coupling factor k is greater than a first threshold value; increasing the rotational speed of the motor by a second amount when the coupling factor k is less than or equal to the first threshold value and greater than a third threshold value, the second amount being smaller than the first amount; decreasing the rotational speed of the motor by a third amount when the coupling factor k is greater than or equal to a fourth threshold value and less than a second threshold value; decreasing the rotational speed of the motor by a fourth amount when the coupling factor k is greater than or equal to a fifth threshold value and less than the fourth threshold value, the fourth amount being larger than the third amount; decreasing the rotational speed of the motor by a fifth amount when the coupling factor k is less than a fifth threshold value, the fifth amount being larger than the fourth amount; or a combination thereof. Optionally, the method may be further configured to keeping the rotational speed of the motor constant when the coupling factor is equal to the second threshold value.

In some embodiments, the rotational speed only begins an adjustment process when the coupling factor k is greater than a first threshold value or less than a second threshold value. In particular, the speed is adjusted as follows:

When it is determined that the coupling factor k is greater than the first threshold value, the controller begins a subroutine where it increases the rotational speed of the motor in steps until the coupling factor k is below a predetermined value. In particular, during the subroutine, the rotational speed of the motor is increased by a first amount when the coupling factor k is greater than the first threshold value and increased by a second amount when the coupling factor k is less than or equal to the first threshold value but above a third threshold value, after which the pressures are measured, and a coupling factor is determined. This cycle repeats until the coupling factor k is determined to be less than or equal to the third threshold value, at which point it exits this subroutine and returns to monitoring the coupling factor and only adjusting when the coupling factor is greater than the first threshold value or less than the second threshold value.

When it is determined that the coupling factor k is less than the second threshold value, the controller begins a subroutine where it decreases the rotational speed of the motor in steps until the coupling factor k is above a predetermined value. In particular during the subroutine, the rotational speed of the motor is decreased by a third amount when the coupling factor k is greater than or equal to the second threshold value and less than the fourth threshold value; decreased by a fourth amount when the coupling factor k is greater than or equal to the fifth threshold value and less than the second threshold value, the fourth amount being greater than the third amount; and/or decreased by a fifth amount when the coupling factor k is less than a fifth threshold value, after which the pressures are measured, and a coupling factor is determined. This cycle repeats until the coupling factor k is determined to be less than or equal to the third threshold value, at which point it exits this subroutine and returns to monitoring the coupling factor and only adjusting when the coupling factor is greater than the first threshold value or less than the second threshold value.

In some embodiments, the speed is adjusted repeatedly in a predetermined time interval t (such as, e.g., between every 5 and 20 seconds, or 10 seconds).

In some embodiments, the coupling factor k is determined in a second predetermined time interval (which may be, e.g., between every 1 and 5 seconds, such as 2 seconds).

As described herein, the coupling factor k is a quotient of an average of the detected or determined left ventricular pressure value and of an average of the detected or determined aortic pressure value. In some embodiments, an average of the detected or determined left ventricular pressure value and an average of the detected or determined aortic pressure value is determined over a third predetermined time interval (which may be, e.g., between 8 and 12 seconds, such as 10 seconds).

In some embodiments, the first threshold value is 0.75, the second threshold value is 0.55, the third threshold value and the fourth threshold value are 0.65, and the fifth threshold value is 0.15.

In some embodiments, the first threshold value is a target coupling factor k value plus a defined value, the second threshold value is the target coupling factor k value minus the defined value, the third target coupling factor k and the fourth target coupling factor k are the target coupling factor k value, and the fifth threshold value is a value that is 15%-35% of the target coupling factor k value.

In some embodiments, when the speed of the motor is adjusted by different amounts, the second amount and third amount are 0.8-1.9% of an operating range (which may be, e.g., between 12,000 rpm and 22,000 rpm, determined as the difference between the maximum operating speed and minimum operating speed that the processor is configured to provide control within) of the rotational speed of the motor within which the processor is configured to perform the first selectable operating mode, the first amount and fourth amount are 2-4.5% of the operating range, and the fifth amount is 8-19% of the operating range.

According to one embodiment, the method may include detecting suction events, and responding to such suction events by: causing the rotational speed of the motor to decrease by a fifth amount if a first suction event is detected, causing the rotational speed of the motor to decrease by a sixth amount if a second suction event is detected, and reducing an upper limit of the rotational speed of the motor by the sixth amount for a first period of time (such as, e.g., between 10 minutes and 30 minutes, such as 20 minutes) after the second suction event is detected within a predetermined window of time. This predetermined window of time may be between 30 seconds and 5 minutes, and in one embodiment, is 2 minutes.

The method also may include: detecting whether an ECMO device is operably connected to the controller and preventing the selection or performance of the first selectable operating mode if the ECMO device is not detected; receiving a selection from a user interface indicating the processor should operate the blood pump using the first selectable operating mode; or a combination thereof.

In some embodiments, the method also provides for controlling the blood pump only if the pressure readings are reliable. Specifically, the method may also include determining if the detected or determined aortic pressure value, the detected or determined left ventricular pressure value, or both are unreliable; and stopping performance of the method if the detected or determined aortic pressure value, the detected or determined left ventricular pressure value, or both are determined to be unreliable for more than a second period of time (such as between 30 seconds and 5 minutes, and, in some embodiments between 1 minutes and 3 minutes, such as 2 minutes).

In some embodiments, the method also provides for situations where the coupling factor k is very low. Specifically, the method may also comprise causing an alarm notification to be activated when the coupling factor k falls below the fifth threshold value, until the coupling factor k is determined to be greater than or equal to a sixth threshold value (such as, e.g., a value between 20% and 50% of a target coupling factor k value), the sixth threshold value being greater than the fifth threshold value and less than the fourth threshold value.

DETAILED DESCRIPTION

VA-ECMO with VAD support has been tested for the treatment of cardiogenic shock or other forms of hemodynamic deterioration, where the ECMO device maintains systemic circulation and the VAD unloads the left ventricle (sometimes called LV decompression). However, in some instances, in this configuration, the afterload of the heart may be increased, as the ECMO returns the blood back into the descending aorta, i.e., in reverse direction of the common blood flow. Due to the increased afterload, the heart may need to work much harder to overcome the pressure difference between left ventricle and aorta.

The performance of VADs may be challenged by these new conditions, such as by decoupling of the aortic and left ventricular pressure and higher afterload. These two changes may impact the function of the safety features of the devices, such as the suction detection features, which are based on the differential pressures, the aortic pressure, and its pulsatility. Although unloading the left ventricle, the decoupling may cause suction detection features to trigger suction alarms, of which some may be false positives, resulting in an automatic speed reduction when speed is controlled automatically, reduced LV unloading by manual reduction of the speed, or continuous suction alarming (leading to noise/alarm fatigue). In addition, due to the high afterload, it may be difficult to manually find the best speed for the pump to, e.g., avoid suction, leading to these same issues.

In view of the above, the inventors have recognized the benefits of a controller for a blood pump, such as a catheter-based intravascular blood pump, that is capable of being used in conjunction with an ECMO device. As described herein, the controller includes particular startup and operating modes to control the speed of a motor of the blood pump based on a coupling factor k.

Figure 1:
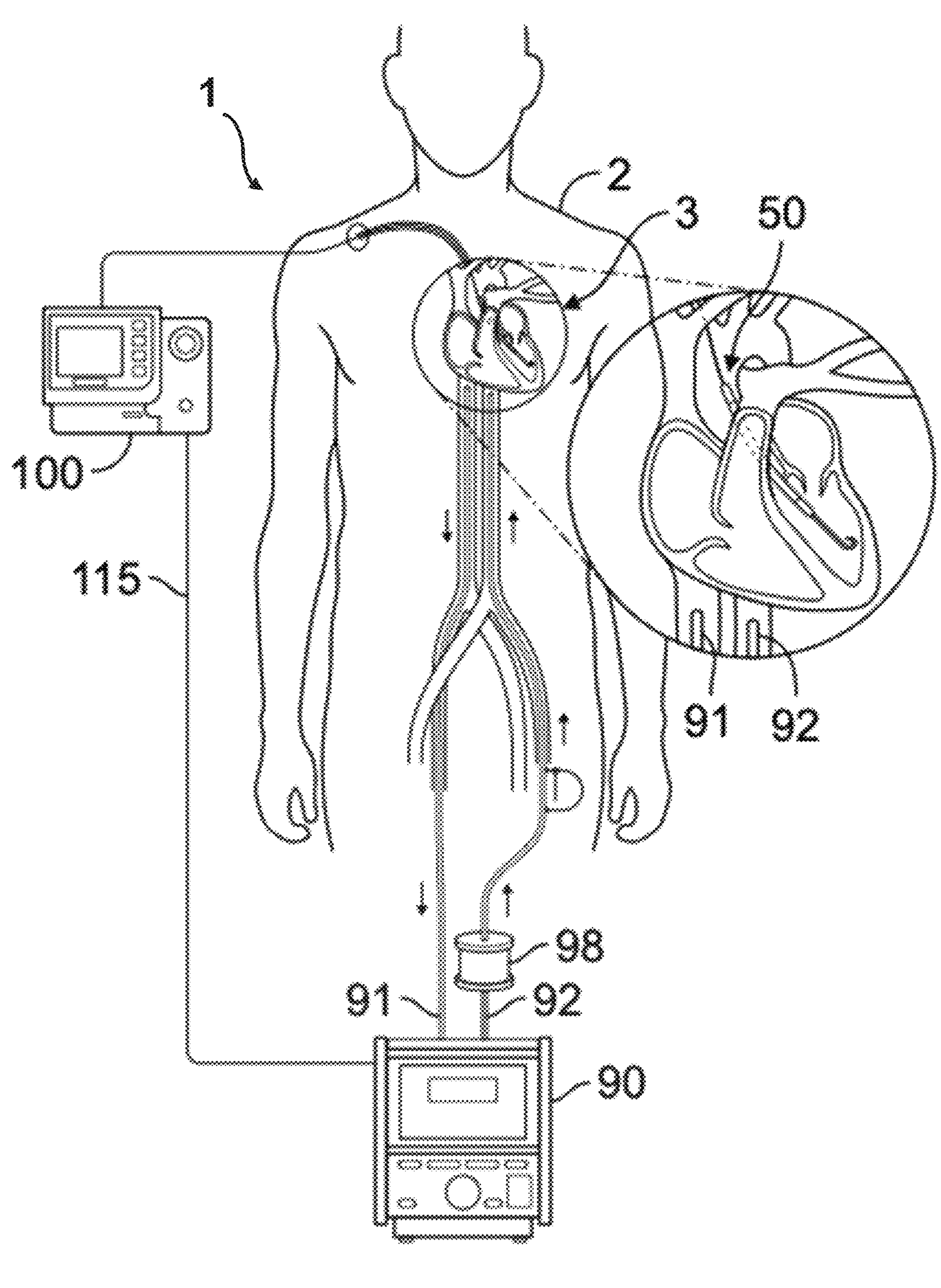
FIG. 1 is a schematic illustration of an embodiment of a disclosed controller in use as part of a system for providing ventricular assistance support of extracorporeal membrane oxygenation.

As seen in reference to FIG. 1, a system 1 for such treatment according to the present disclosure may include a controller 100, a blood pump 50, an ECMO device 90 and an optional separate oxygenator 98. Both the ECMO device 90 and the blood pump 50 may impact the flow of blood in the heart 3 of a patient 2. The ECMO device, as shown, may have an input 91 and output 92 for blood flow, the output 92 for providing blood to the heart 3. The blood pump 50 is shown here with a distal-most portion in a left ventricle of the heart 3, and a more proximal portion in the aorta, configured to move blood from the left ventricle to the aorta through a flow cannula. The blood pump 50 is a catheter-based intravascular blood pump. The ECMO device 90 may be in communication with the controller 100 via, e.g., one or more communication cables 115.

While the controller 100 and the ECMO device 90 are shown in FIG. 1 as two separate devices, in some embodiments, the functions of the ECMO device and the functions of the controller may be combined into a single unit (e.g., controller 100) capable performing the ECMO process as well as controlling the blood pump 50.

It is understood that while FIG. 1 shows the ECMO device and tubing configured for VA-ECMO, the ECMO device could readily be replaced or reconfigured in other ECMO approaches, including, e.g., VVA-ECMO.

Figure 2:
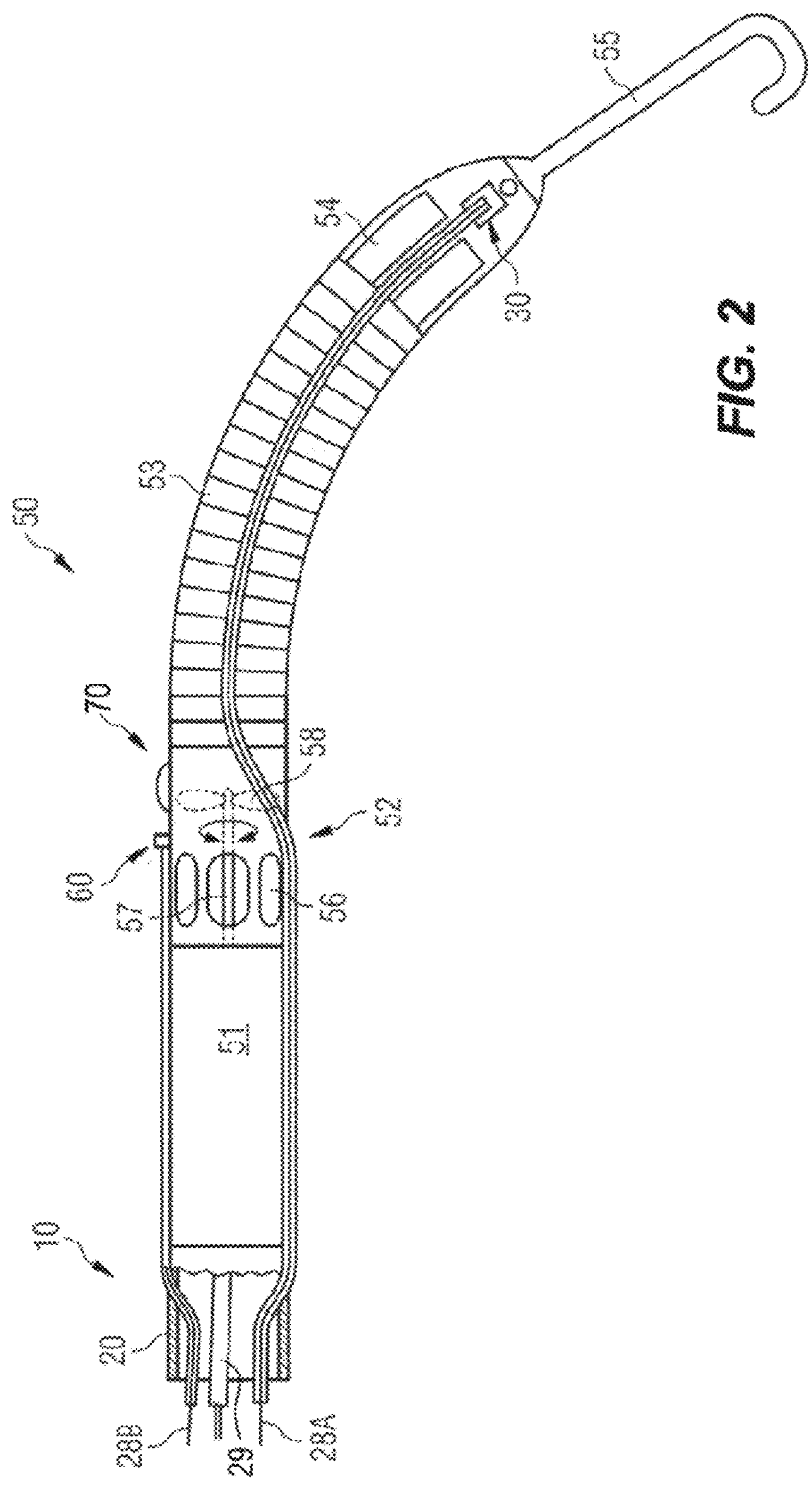
FIG. 2 is an illustration of a distal portion of an embodiment of a catheter-based intravascular blood pump.

An example of a blood pump 50 can be understood with reference to FIG. 2. Specifically, FIG. 2 shows a catheter-based intravascular blood pump (sometimes referred as "blood pump"), which is described herein as one exemplary embodiment of a VAD.

The blood pump 50 comprises a catheter 10, by means of which the blood pump 50 is temporarily introduced through the aorta and the aortic valve into the left ventricle of a heart. As shown in more detail in FIG. 2, the blood pump also includes a rotary pumping device 70 fastened to the end of a catheter tube 20. The rotary pumping device 70 may include a motor section 51 and a pump section 52 located at an axial distance therefrom. A flow cannula 53 may be connected to the pump section 52 at a first end, extend from the pump section 52, and have an inflow cage 54 located at a second, opposite end. The inflow cage 54 may have attached thereto a soft and flexible atraumatic tip 55. The pump section 52 may include a pump housing having outlet openings 56. Further, the pumping device 70 may include a drive shaft 57 protruding from the motor section 51 into the pump housing of the pump section 52. Via a drive shaft 57, an electric motor of the motor section 51 may drive an impeller 58 as a thrust element by means of which, during operation of the rotary pumping device 70, blood can be sucked through the inflow cage 54 and discharged through the outlet openings 56.

The rotary pumping device 70 can also pump in the reverse direction when adapted accordingly, e.g., as required when the blood pump 50 is placed in the right heart. In this regard and for the sake of completeness, FIG. 1 shows the blood pump 50 as one particular example of a VAD located in and for assistance of the left heart.

In FIG. 2, three lines, two signal lines 28A and 28B and a power-supply line 29 for supplying an electrical current to the motor section 51, may pass through the catheter tube 20 of the catheter 10 to the pumping device 70. The two signal lines 28A, 28B and the power-supply line 29 may be attached at their proximal end to controller 100. It is understood that there may be additional lines for further functions in other embodiments. For example, a line for a purge fluid (not shown) may pass through the catheter tube 20 of the catheter 10 to the pumping device 70 as well. Additional lines may be added based on different sensing technologies.

As shown in FIG. 2, the signal lines 28A, 28B may be part of blood pressure sensors with corresponding sensor heads 30 and 60, respectively, which are located externally on the housing of the pump section 52. The sensor head 60 of the first pressure sensor may be associated with signal line 28B. The signal line 28A may be associated with and connected to the sensor head 30 of the second blood pressure sensor. The blood pressure sensors may, for example, be optical pressure sensors functioning according to the Fabry-Perot principle as described in U.S. Pat. No. 5,911,685 A, wherein the two signal lines 28A, 28B are optical fibers. However, other pressure sensors may be used instead. Basically, signals of the pressure sensors, which carry the respective information on the pressure at the location of the sensor and which may be of any suitable physical origin, e.g., of optical, hydraulic, or electrical etc. origin, may be transmitted via the respective signal lines 28A, 28B to corresponding inputs of a data processing unit 110 of the control device 100. In the example shown in FIG. 1, the pressure sensors may be arranged so that the aortic pressure AOP is measured by sensor head 60 and the left ventricular pressure LVP is measured by sensor head 30.

The controller may be connected via input ports with the respective signal lines 28A, 28B to receive the corresponding measuring signals $AOP_{meas}$ for the aortic pressure AOP and $LVP_{meas}$ the left ventricular pressure LVP.

Figure 3:
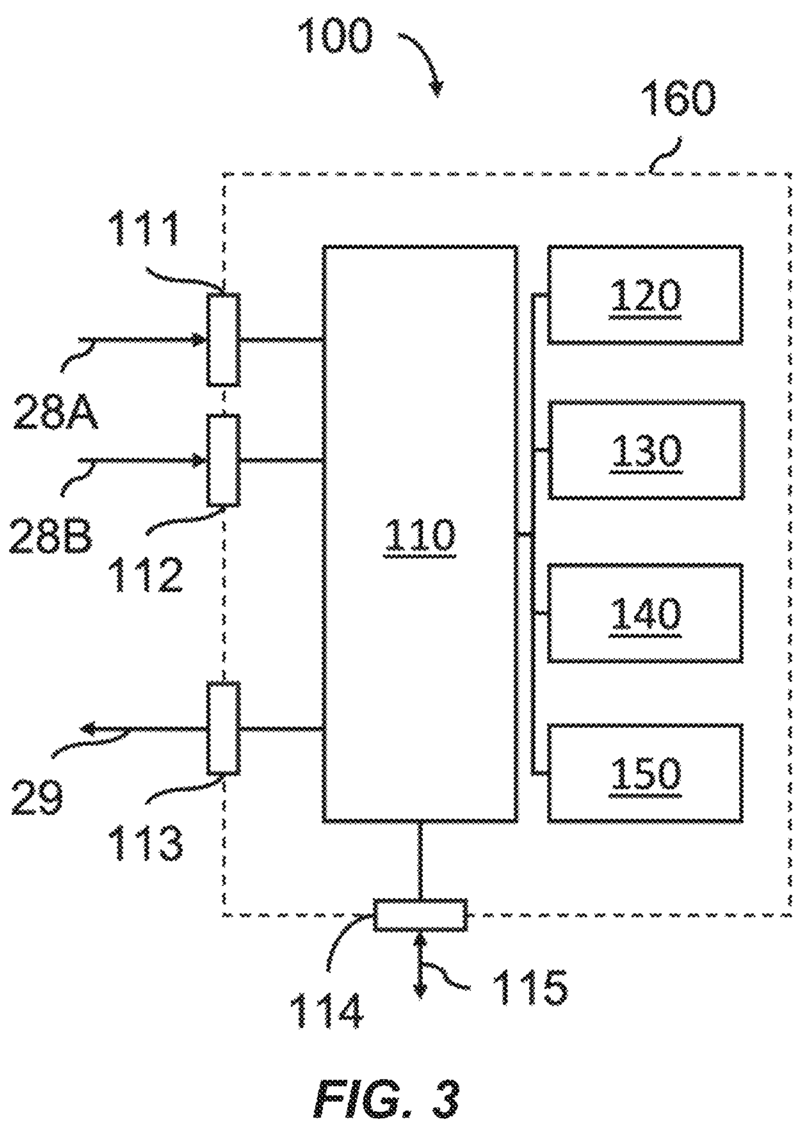
FIG. 3 is a block diagram of a disclosed controller.

An example of a controller can be understood with reference to FIG. 3. Specifically, a controller 100 may comprise several components. The first component may include one or more processors 110 (which includes associated non-transitory computer-readable media that contain instructions for controlling the processor). The controller 100 may contain various ports 111, 112, 113, 114 that are operably connected to the processor 110, for receiving signals from various other components of the system, and/or sending signals to other components of the system. Not shown are various filters, converters, etc., that may allow the signals to be coded, decoded, formatted, or otherwise modified as appropriate in order to be read or sent by the controller. The controller 100 may contain at least one port 111, 112, 113 that operably connects the processor with a blood pump 50. In some embodiments, the controller 100 may include one or more input ports 111, 112 for receiving pressure signals from two or more pressure sensors, such as pressure sensors connected to the controller via, e.g., optical fibers 28A, 28B, measuring pressures in different chambers of a heart, and a port 113 for, e.g., a power-supply line 29 for supplying an electrical current to the motor section 51 of the blood pump 50. In some embodiments, the controller 100 may contain an additional port 114 that is configured to operably connect the processor 110 with an extra-corporeal membrane oxygenation (ECMO) system, such as a VA-ECMO system, via, e.g., communication cable 115 or some other appropriate additional line.

The one or more processors 110 may be configured for acquiring external and internal signals for signal processing, such as calculation of a difference between two pressure signals as a basis for estimating pump flow, for signal analysis, such as deriving an actual value of an at least one characteristic parameter a, such as the end-diastolic left ventricular pressure EDLVP or a filling gradient FG of the heart which then may be used to control a motor speed of the blood pump, i.e. a rotational speed of the motor of the motor unit 51 of the blood pump 50.

The controller 100 may also contain other components. In some embodiments, the one or more processors 110 may be configured to control a display 130, such as a touch-sensitive display. In some embodiments, the one or more processors 110 may be configured to control an audio speaker 140 (e.g., to create an auditory alarm, etc.). In some embodiments, the one or more processors 110 may be configured to receive input from one or more buttons or switches 150.

In some embodiments, the controller may include a housing 160 configured to contain (within an internal volume of space defined by outer walls of the housing) at least the processor 110. In some embodiments, the walls of the housing may define a plurality of openings therethrough. In some embodiments, at least a portion of the display 120 may be present in at least one of the plurality of openings in the housing 160. In some embodiments, a display may be operably connected to the processors 110, but not within or attached to the housing 160.

Figure 4:
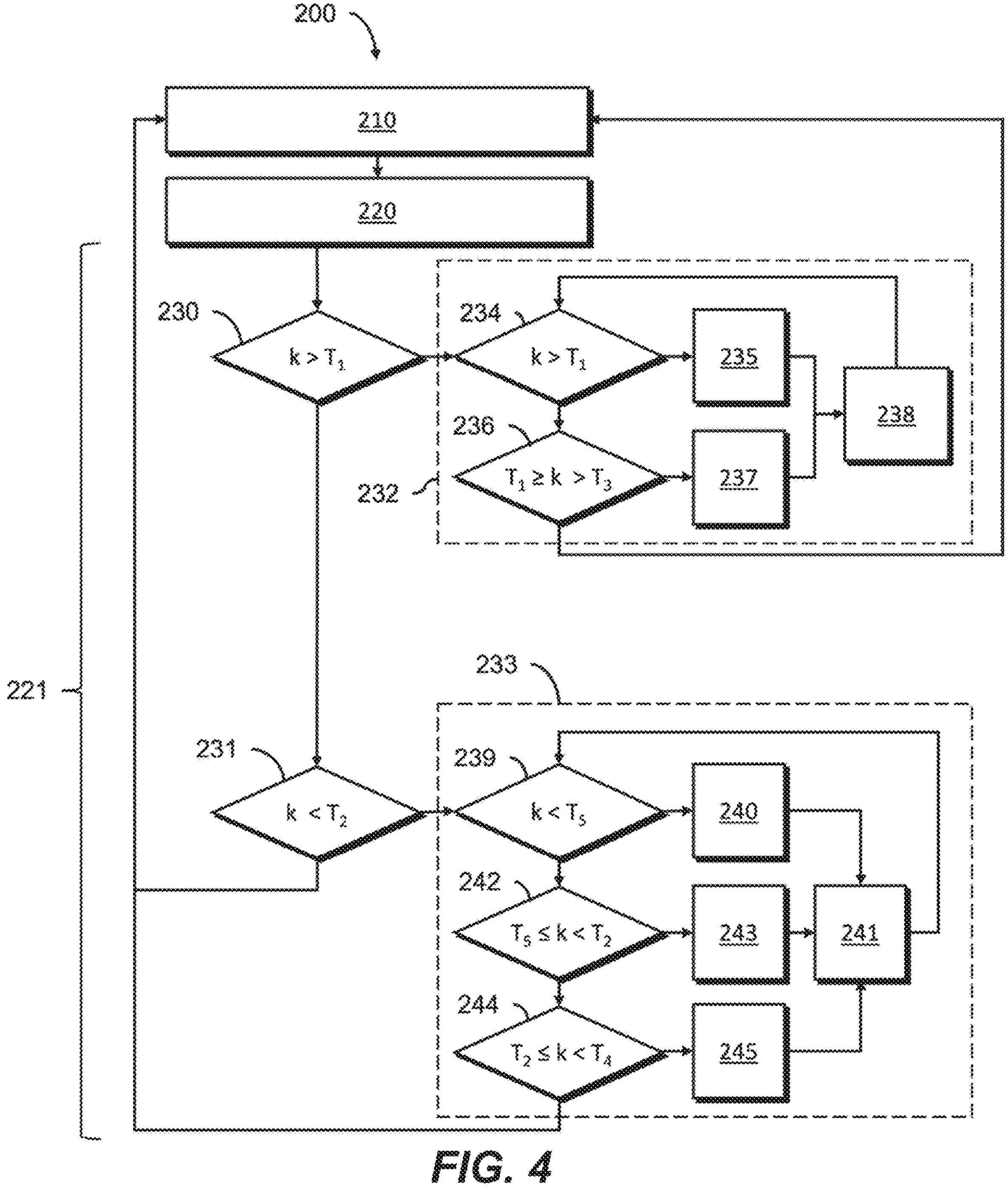
FIG. 4 is a flowchart of an embodiment of a first selectable operating mode.

In some embodiments, the controller 100 may comprise a processor 110 configured to control a rotational speed of a motor of the blood pump 50 using a first selectable operating mode. An embodiment of the first selectable operating mode is illustrated in FIG. 4. There, the method 200 comprises a first step of detecting or determining pressures 210.

In one embodiment, the first step comprises detecting or determining two pressure values—a left ventricular pressure value and an aortic pressure value. For purposes herein, the detected or determined left ventricular pressure value is the peak of the detected or determined left ventricular pressure value ($LVP_{max}$). Also, for purposes herein, the detected or determined aortic pressure value is the peak of the detected or determined aortic pressure value ($AOP_{max}$).

These values may be measured based on signals provided by pressure sensors, e.g., on the blood pump 50. In some embodiments, the signals the processor 110 receives from the pressure sensors may be utilized as a variable in a calculation that determines the left ventricular or aortic pressure value.

These values may be detected or determined at frequencies of, e.g., 0.2 Hz or greater or 0.5 Hz or greater.

In some embodiments, the second step 220 of the first selectable operating mode is to determine a coupling factor k using the detected or determined left ventricular and aortic pressure values. In particular, the coupling factor k includes a quotient of an average of at least some of the detected or determined left ventricular pressure values and of an average of at least some of the detected or determined aortic pressure values at a predetermined time interval. In some embodiments, this predetermined time interval may be between 1 and 5 seconds, such as 2 seconds. That is, in some embodiments, k is determined every 2 seconds.

In some embodiments, $LVP_{max}$ and $AOP_{max}$ are determined every 1-5 seconds, such as ever 2 seconds. $LVP_{max}$, mean and $AOP_{max}$, mean may then be determined by taking the mean of the previous 2 to 10 $LVP_{max}$ and $AOP_{max}$ consecutive determinations, respectively. In some embodiments, $LVP_{max, mean}$ and $AOP_{max, mean}$ may be determined by taking the mean of the previous 5 consecutive $LVP_{max}$ and $AOP_{max}$ determinations, respectively. The coupling factor k may then be calculated as $k=LVP_{max, mean}/AOP_{max, mean}$.

In one embodiment, the average of the detected or determined left ventricular pressure value and the average of the detected or determined aortic pressure value that are used to determine the coupling factor are themselves determined over a different predetermined time interval than the time period use for determining k. In some embodiments, this different time interval may be between 8 and 12 seconds, such as 10 seconds.

Figure 5:
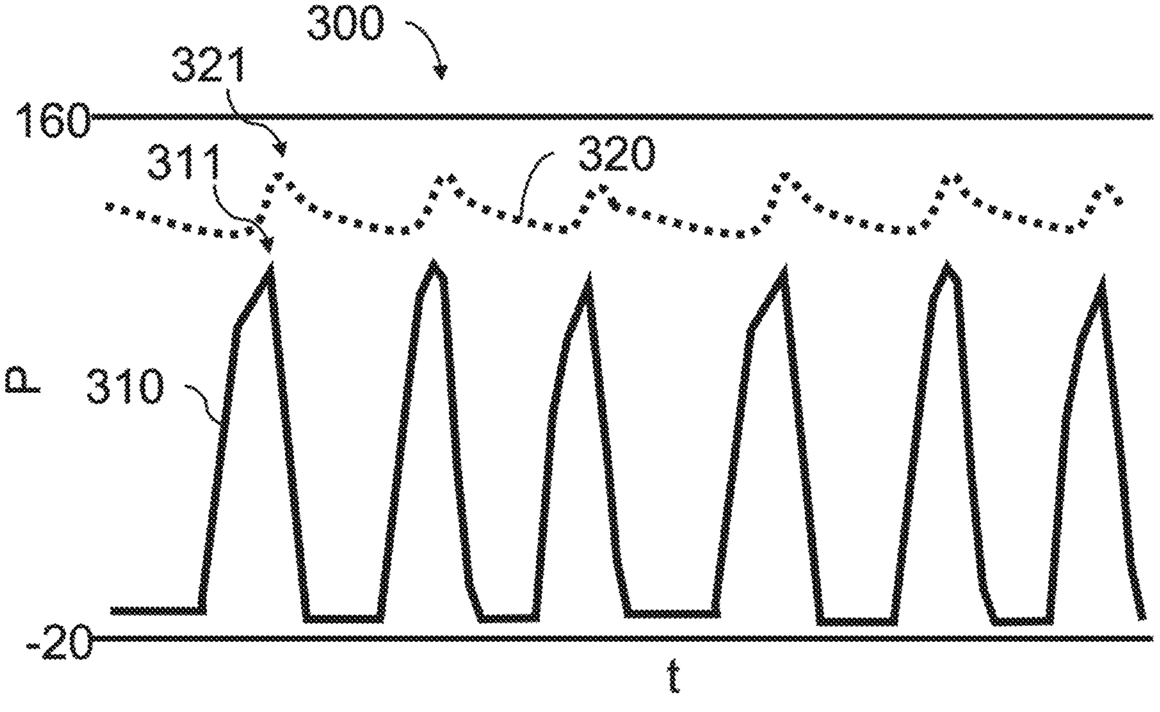
FIG. 5 is a representative illustration of a display of detected or determined pressures used for calculating a coupling factor k.

FIG. 5 shows a schematic of a graphical display 300 of the left ventricular and aortic pressures are shown as it might appear on a display screen of the controller. The left ventricular pressure 310 and aortic pressure 320 are shown as measured over time. A peak value of the left ventricular pressure 311 is shown, as is a peak value of the aortic pressure 321. These two values (311, 321) may be used to calculate the coupling factor k. Using the graphs shown in FIG. 5, the value of the coupling factor k would be less than 1.

Referring back to FIG. 4, after determining the coupling factor k, the method 200 used by the one or more processors 110 may involve adjusting the rotational speed of the motor based on the determined value of the coupling factor k. As is understood in the art, this "adjusting" may include indirect adjustment, where processor 110 is configured to send a signal to one or more other components or modules that then perform some action based on the signal, thereby adjusting the speed of the motor.

The processor 110 may be configured to adjust the rotational speed of the motor in the first selectable operating mode within a predetermined time interval. In some embodiments, this predetermined time interval may be between every 5 and 20 seconds.

In some embodiments, the controller 100 may be configured to adjust the motor speed based on the value of the coupling factor k every 10 seconds. For example, in one embodiment, the coupling factor k is determined every 2 seconds based on detected/determined pressure values over the previous 2 seconds, and every 5th value of the coupling factor k that is determined, the speed is adjusted based on that 5th value of the coupling factor k.

In some embodiments, the processor 110 may be configured to adjust the rotational speed of the motor in the first selectable operating mode only after a predetermined time interval has occurred since the previous speed adjustment. In some embodiments, the coupling factor k is calculated every 1-5 seconds, such as every 2 seconds, but the coupling factor k is only used every 5-20 seconds, such as every 10 seconds, after the speed was previously adjusted.

As seen in FIG. 4, after determining the coupling factor k, the speed may then be adjusted 221 based on the value of the coupling factor k. In one embodiment, this may be done by comparing the coupling factor k to various threshold values ($T_1, T_2, \ldots, T_n$). In some embodiments, the threshold values define ranges of the coupling factor k corresponding to specific kinds of motor speed adjustments.

In some embodiments, the control system is designed around a target coupling factor value or range of target coupling factor values. When the coupling factor k value is below the target k value(s), the rotational speed of the motor may be automatically increased, and when the coupling factor k value is above the target k value(s), the rotational speed of the motor may be automatically decreased.

In some embodiments, at least one speed adjustment is made based on the determined value of the coupling factor k, where the at least one adjustment comprises or consists of: increasing the rotational speed of the motor by a first amount when the coupling factor k is greater than a first threshold value; increasing the rotational speed of the motor by a second amount when the coupling factor k is less than or equal to the first threshold value and greater than a third threshold value, the second amount being smaller than the first amount; decreasing the rotational speed of the motor by a third amount when the coupling factor k is greater than or equal to a fourth threshold value and less than a second threshold value; decreasing the rotational speed of the motor by a fourth amount when the coupling factor k is greater than or equal to a fifth threshold value and less than the fourth threshold value, the fourth amount being larger than the third amount; decreasing the rotational speed of the motor by a fifth amount when the coupling factor k is less than a fifth threshold value, the fifth amount being larger than the fourth amount; or a combination thereof. Optionally, the first selectable operating mode may be further configured to keeping the rotational speed of the motor constant when the coupling factor is equal to the third threshold value. A simplified descriptions of such an approach can be seen in Table 1, below.

TABLE 1

(Example of possible k value ranges and associated rotational speed adjustments)

| k value range | Speed Adjustments |
|---|---|
| Somewhat higher than target k | Moderate Speed Increase ($1^{st}$ Amount) |

TABLE 1-continued

| (Example of possible k value ranges and associated rotational speed adjustments) | |
|---|---|
| k value range | Speed Adjustments |
| value(s) | |
| A little higher than target k value(s) | Small Speed Increase (2nd Amount, smaller than 1st Amount) |
| (Optionally) Target k value(s) | No Adjustment |
| A little lower than target k value(s) | Small Speed Decrease (3rd Amount) |
| Somewhat lower than target k value(s) | Moderate Speed Decrease (4th Amount, Larger than 3rd Amount) |
| Much lower than target k value(s) | Large Speed Decrease (5th Amount, Larger than 4th Amount) |

In some embodiments, no speed adjustments are made if the coupling factor is between a first threshold value (or upper limit) and a second threshold value (or lower limit) ($T_1$, $T_2$). That is, after the second step 220, if the value of coupling factor k is between $T_1$ and $T_2$ (as used herein, "between" is intended to be inclusive of the upper and lower limits), no action is taken. These upper and lower limits may be centered around a target range for the coupling factor k defined by two threshold values ($T_3$, $T_4$) or centered around a common target value for the coupling factor k (i.e., where $T_3=T_4$) value defined by common threshold value.

The amount of the speed increase or decrease can depend on how close to the target coupling factor k value the determined coupling factor k is, and whether the coupling factor k is greater or less than the target coupling factor k. Simplified descriptions of such an approach can be seen in Tables 2 and 3, below.

TABLE 2

| (Adjustments Made Once Coupling Factor is Determined To Be Greater than First Threshold Value | |
|---|---|
| Coupling factor k value range | Speed Adjustment |
| Somewhat higher than target coupling factor k value(s) ($k > T_1$) | Moderate Speed Increase (1st Amount) |
| A little higher than target coupling factor k value(s) ($T_1 \geq k > T_3$) | Small Speed Increase (2nd Amount, smaller than 1st Amount) |
| At or below target coupling factor k value(s) ($k \leq T_3$) | No Adjustment, stop making adjustments until $k > T_1$ or $k < T_2$. |

TABLE 3

| (Adjustments Made Once Coupling Factor is Determined To Be Less than Second Threshold Value | |
|---|---|
| Coupling factor k value range | Speed Adjustment |
| At or above Target coupling factor k value(s) ($k \geq T_4$) | No Adjustment, stop making adjustments until $k > T_1$ or $k < T_2$ |
| A little lower than target coupling factor k value(s) ($T_2 \leq k < T_4$) | Small Speed Decrease (3rd Amount) |
| Somewhat lower than target coupling factor k value(s) ($T_5 \leq k < T_2$) | Moderate Speed Decrease (4th Amount, Larger than 3rd Amount) |
| Much lower than target coupling factor k value(s) ($k < T_5$) | Large Speed Decrease (5th Amount, Larger than 4th Amount) |

The above descriptions and approach are intended to be non-limiting. As is seen in Tables 1 and 2, if the determined value of the coupling factor k is greater than the first threshold value, the controller attempts to increase the rotational speed, in steps, to attempt to lower the coupling factor k until it is less than or equal to the target value or target range of values. If the value is less than the second threshold value, the controller attempts to decrease the rotational speed, in steps, to attempt to increase the coupling factor k until it is greater than or equal to the target value or target range of values.

In some embodiments, the first threshold value $T_1$ is a target coupling factor k value plus a defined value (such as 0.1, 0.15, or 0.2), the second threshold value $T_2$ is the target coupling factor k value minus that defined value, the third threshold value $T_3$ and the fourth threshold value $T_4$ are the target coupling factor k value, and the fifth threshold value $T_5$ is a value that is 15%-35% of the target coupling factor k value. As a simple example, if the coupling factor k is 0.7, the defined value is 0.15, and the fifth threshold value is 20% of the target coupling factor k, then the controller 110 could be configured to begin increasing the speed when the coupling factor k>0.85, at which time the speed would be increased with moderate speed increases when k>0.85, smaller speed increases when the coupling factor k was between 0.7 and 0.85, and the speed increases would stop after the coupling factor k reached 0.7 or below. The controller would be configured to begin decreasing the speed when the coupling factor k was less than 0.55, at which time the speed would be decreased with a large speed decrease when k<0.14, a moderate speed decrease when k was between 0.14 and 0.55, and the speed decreases would stop after the coupling factor k reached 0.7 or above.

In one embodiment, the first threshold value is 0.75, the second threshold value and fifth threshold value are 0.65, the third threshold value is 0.15, and the fourth threshold value is 0.55.

In some embodiments, the amount of speed adjustment may be based on the operating speed range of the motor (e.g., the difference between the maximum and minimum speeds the motor is designed to run in the first selectable operating mode). That is, if the motor is designed to be controlled in this operating mode when rotating between, e.g., 31,000 rpm and 46,000 rpm, the operating speed range may be 15,000 rpm. In some embodiments, this range may be between 12,000 rpm and 22,000 rpm. In some embodiments, the small speed increases (the second amount) and/or decreases (the third amount) may be an amount that is between 0.8% and 1.9% of that operating range, the moderate speed increases and/or decreases (first and fourth amounts) may be an amount that is between 2% and 4.5% of that operating speed, and the large speed decrease (the fifth amount) may be an amount that is between 8% and 19% of that operating speed.

In some embodiments, the first amount of speed adjustment (i.e., the absolute amount) is equal to the fourth amount (i.e., the absolute amount). In some embodiments, the second amount of speed adjustment (i.e., the absolute amount) is equal to the third amount (i.e., the absolute amount).

In one embodiment, the second and third amounts are 200 rpm, the first and fourth amounts are 500 rpm, and the fifth amount is 2000 rpm.

FIG. 4 illustrates a speed adjustment process 221 the processor 110 is configured to use in some embodiments. In the speed adjustment process 221, the speed is only adjusted if the coupling factor k is determined to be greater than a first threshold value ($T_1$) 230 or the coupling factor k is determined to be less than a second threshold value ($T_2$) 231. If the coupling factor k is between the first threshold value ($T_1$) and the second threshold value ($T_2$), the speed adjustment process is essentially ignored, and steps 210 and 220 are repeated.

Once the coupling factor k is determined to be greater than a first threshold value 230, a first subprocess 232 is entered into, whereby (as disclosed previously), the speed is increased until the coupling factor is less than a third threshold value ($T_3$). Specifically, in the first subroutine 232, if the coupling factor k is greater than a first threshold value ($T_1$) 234, then the rotational speed of the motor may be increased by a first amount 235; the rotational speed of the motor may be increased by a second amount 237 when the coupling factor k is less than or equal to the first threshold value ($T_1$) and greater than a third threshold value ($T_3$) 236. The second amount of motor speed increase (i.e., the absolute value of the change in motor speed caused by the second amount) may be smaller than the first amount (i.e., the absolute value of the change in motor speed caused by the first amount). After the speed adjustments (235, 237) are made, the pressures are measured, and the coupling factor k is determined again 238 as described previously for steps 220 and 221. This subprocess 232 is repeated until the coupling factor k is less than or equal to the third threshold value ($T_3$), at which time the subprocess 232 ends and the process returns to measuring pressures in step 210.

Once the coupling factor k is determined to be less than a second threshold value 231, a second subprocess 233 is entered into, whereby (as disclosed herein), the speed is decreased until the coupling factor is greater than a fourth threshold value ($T_4$), which may be the same as the third threshold value ($T_3$) in some embodiments. Specifically, in the second subroutine 233, if the coupling factor k is less than the fourth threshold value ($T_4$) and greater than or equal to the second threshold value ($T_2$) 244, the rotational speed of the motor may be decreased by a third amount 245; the rotational speed of the motor may be decreased by a fourth amount 243 when the coupling factor k is greater than or equal to a fifth threshold value ($T_5$) and less than the second threshold value ($T_2$) 242; and if the coupling factor k is less than the fifth threshold value ($T_5$) 239, the rotational speed of the motor may be decreased by a fifth amount 240. The fourth amount of motor speed decrease (i.e., the absolute value of the change in motor speed caused by the fourth amount) may be smaller than the decrease of fifth amount (i.e., the absolute value of the change in motor speed caused by the fifth amount). The third amount of motor speed decrease (i.e., the absolute value of the change in motor speed caused by the third amount) may be smaller than the fourth amount of motor speed decrease (i.e., the absolute value of the change in motor speed caused by the fourth amount). After the speed adjustments (240, 243, 245) are made, the pressures are measured, and the coupling factor k is determined again 241 as described previously for steps 220 and 221. This subprocess 233 is repeated until the coupling factor k is greater than or equal to the fourth threshold value ($T_4$), at which time the subprocess 233 ends and the process returns to measuring pressures in step 210.

Figure 6:
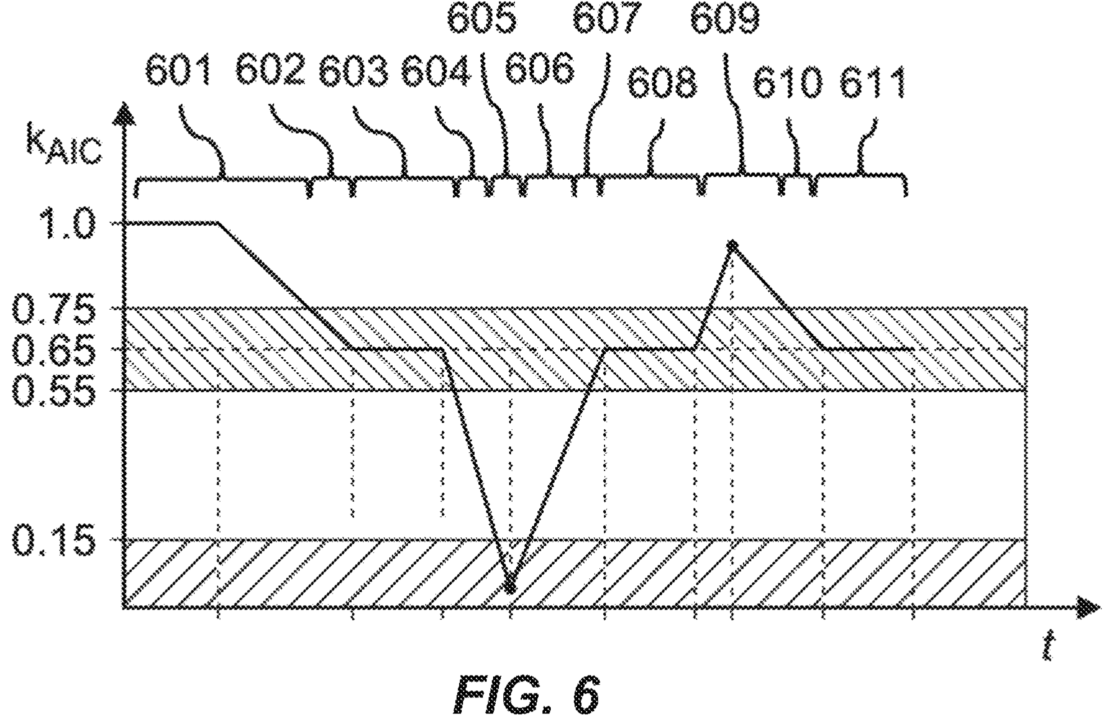
FIG. 6 is a graphical depiction of the values of a rotational speed of a motor of a catheter-based intravascular blood pump ($N_{set}$, bottom chart) changing with relationship to values of the coupling factor ($k_{AIC}$, top chart).

This can be seen graphically with reference to FIG. 6. As seen in this figure, near the beginning, where the value of the coupling factor k is between 1 and 0.75 601, the motor speed increases, in steps, each step (e.g., after each time the coupling factor k is re-calculated based on updated pressures) a moderate amount of speed increase until the value of the coupling factor k is determined to be between 0.75 and 0.65 602, where the speed increase with each step drops to a smaller amount. Once the coupling factor k reaches 0.65 603, no further speed changes occurs until the coupling factor k falls outside the 0.55-0.75 range. When the coupling factor k suddenly drops towards 0, the speed first decreases each step by a moderate amount when the coupling factor k was determined to be less than 0.55 but greater than 0.15 604, but when the coupling factor k continued to decrease and is determined to be less than 0.15 605, the speed decreases significantly with each step until the coupling factor k is then determined to be above 0.15 and less than 0.55 606, during which time the speed decrease continues, but by only a moderate amount each step. Once the coupling factor k is determined to be between 0.55 and 0.65 607, the speed decrease continues, but only by a small amount each step, until the coupling factor k is once again determined to be at or above 0.65 608. Again, no further speed changes are made until the coupling factor k is above 0.75 609, where the speed increases by a moderate amount each step until the coupling factor k is between 0.75 and 0.66 610, where the speed continues being increased at a smaller amount each step, until the coupling factor k is finally back to at or below 0.65 611.

Figure 7:
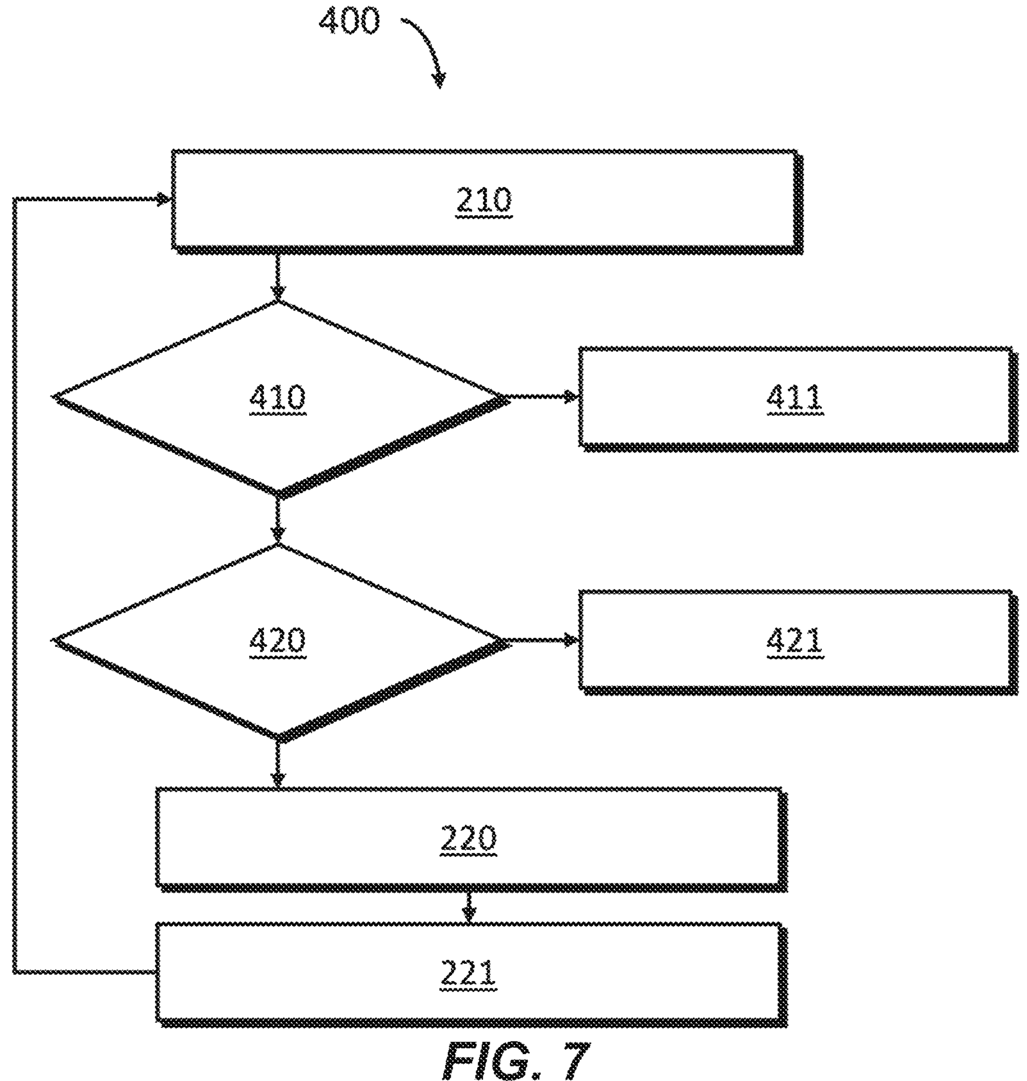
FIG. 7 is a flowchart of an embodiment of various safety features embedded in a first selectable operating mode.

As seen in FIG. 7, the processors 110 may be configured to make other determinations and take corrective actions, if necessary, when certain events occur. The processors may be configured to follow a method 400, where certain safety features may be placed ahead of any of the previously described determination of coupling factors 220 and speed adjustments 221. For example, the processor 110 may be configured to determine if a pump position is incorrect 410 (e.g., the blood pump is in the ventricle, or the blood pump is in the aorta), which may be based on the detected or determined pressures. In such cases, automatic corrective action(s) may be performed 411. This corrective action 411 may comprise, e.g., pausing any speed adjustment as described above, until the incorrect pump position determination is no longer made, at which time the above-described speed adjustment may optionally resume automatically. If the blood pump is correctly placed but a suction event is detected 420, alternate corrective action(s) may automatically be performed 421.

In some embodiments, the processor 110 may be further configured to detect one or more suction events 420, and then respond to such suction events automatically 421. In some embodiments, it may do so by: causing the rotational speed of the motor to decrease by a fifth amount if a first suction event is detected, causing the rotational speed of the motor to decrease by a sixth amount if a second suction event is detected, and reducing an upper limit of the rotational speed of the motor by the sixth amount for a period of time (such as, e.g., between 10 minutes and 30 minutes, or 20 minutes) (sometimes referred to as a “pause”) after the second suction event is detected within a predetermined window of time (such as between 30 seconds and 5 minutes, or 2 minutes).

Figure 8:
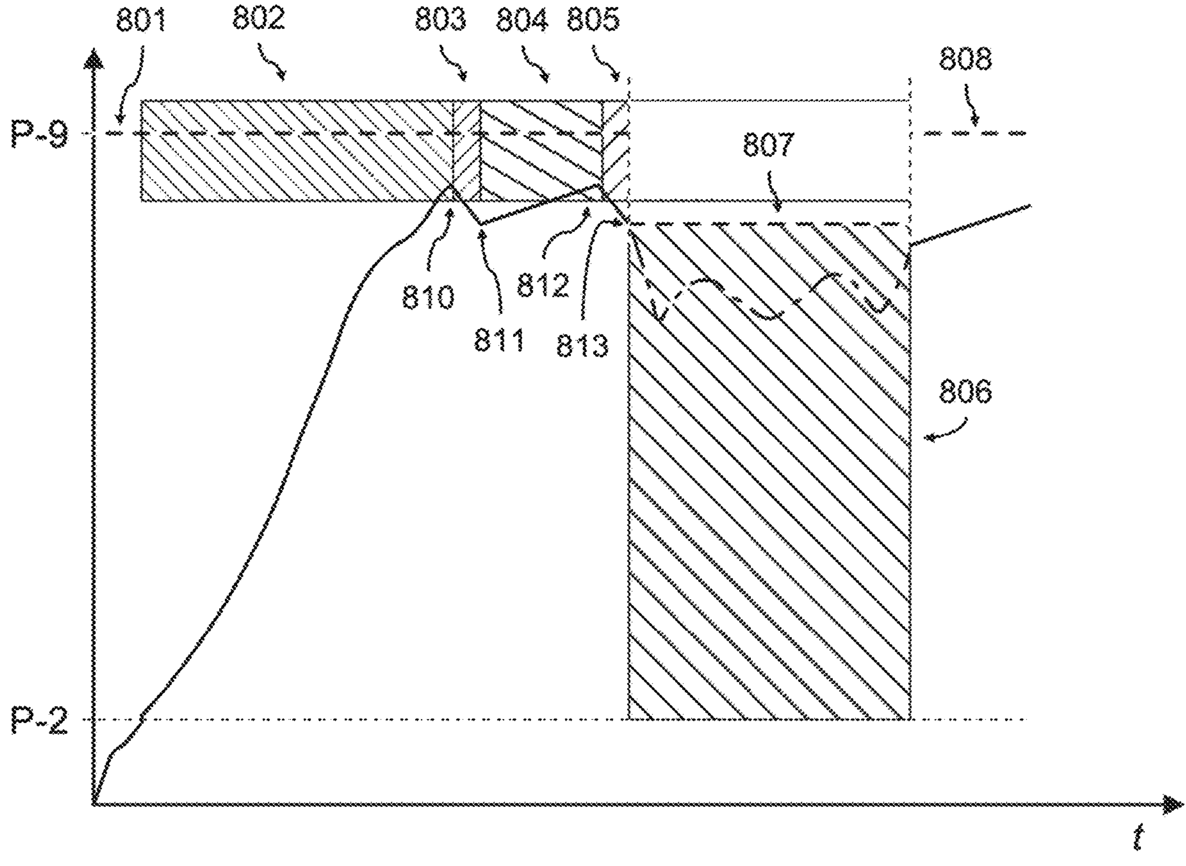
FIG. 8 is a graphical depiction of an example of the rotational speed of a motor of a catheter-based intravascular blood pump being controlled when suction events are detected.

This process is schematically represented in FIG. 8, a graph of the rotational speed of a motor over time. There, as seen, the rotational speed of the motor may be increased from 0, past P-2 (preset speed option #2, around 31,000 rpm) towards the initial maximum allowable speed 801, P-9 (preset speed option #9, around 46,000 rpm). After the rotational speed passes P-2, the device is in the normal operation range of the device. During normal operation, there is a risk of suction 802. Indeed, a first suction event 810 may be detected, and the rotational speed may be promptly decreased 803 while the suction event is being cleared. Once the suction event is cleared 811, the rotational speed may again be increased. However, within a period of time of less than 2 minutes 804, a second event 812 may be detected, at which time the rotational speed may be automatically decreased again 805 until the second suction event is cleared 813. From that time forward, for a period of 20 minutes 806, a new, lower maximum rotational speed 807 may be put into place, that is less than P-9 (the former maximum allowable speed). After 20 minutes, the maximum rotational speed may be raised back to P-9 808, and the motor may begin slowly ramping back up, without a third such suction event occurring.

In some embodiments, if the maximum speed is reduced, an alarm is generated indicating the reduction in rotational speed has occurred.

In some embodiments, if suction is detected during the period of time (e.g., during the 10-to-30-minute window where the maximum rotational speed has been reduced), the rotational speed may be further reduced until suction is clear, the pause counter may be reset and another 10-30-minute pause will start.

In some embodiments, if the pump motor speed reaches the lower speed limit the first selectable operating mode was configured to operate using (e.g., 31,000 rpm), the rotational speed may not decrease further, but an alarm may be triggered. In one embodiment, the alarm is different from the alarm indicating the maximum speed has been reduced.

Given the cooperative work required by the ECMO and VAD to provide the therapy the above-described techniques are useful for, the processor 110 may be configured to: (i) detect whether an ECMO device (e.g., a VA-ECMO or VVA-ECMO device) is operably connected to the controller and/or operating, and prevent the selection or performance of the first selectable operating mode if the ECMO device is not detected and/or operating; (ii) receive a selection indicating the processor should operate the blood pump using the first selectable operating mode; or (iii) both (i) and (ii). In some embodiments, the processor 110 may be further configured only for (i)—that is, unless an ECMO device 90 is detected as being connected and/or operating, a user cannot select the controller 100 to operate in the first selectable operating mode.

In some embodiments, as an alternative, or in addition to, receiving a signal from the ECMO device 90, the controller 100 may be configured to receive a signal from flow controller 99 associated with the ECMO device 90 that is indicative of the ECMO being in operation. For example, in one embodiment, controller 100 may not be allowed to operate in the first selectable operating mode unless it receives a signal from the ECMO device 90 indicating that the ECMO device 90 is connected, and also receives a signal from the flow controller indicating the blood is flowing through the ECMO device 90 and therefore the ECMO 90 device is in operation.

Given a target coupling factor k, a startup process can be implemented by the processor that quickly and safely gets the blood pump 50 up to an appropriate operating speed. This can be described with reference to FIG. 9. To accomplish the startup, the processor 110 may be further configured to perform a startup method 500 prior to performing the first selectable operating mode 200. In some embodiments, the startup method requires first increasing the rotational speed of the motor from zero to a minimum rotational speed 510. This minimum rotational speed should be the lowest rotational speed that the processor 110 is configured to use when performing the first selectable operating mode. In some embodiments, this minimum speed is between 5,000 rpm and 50,000 rpm, such as between 20,000 rpm and 40,000 rpm, or 31,000 rpm.

Once the minimum rotational speed is reached, the processor 110 may then determine the coupling factor k 520 using a detected or determined aortic pressure value and a detected or determined left ventricular pressure value, just as described above, where the coupling factor k is a quotient of an average of the detected or determined left ventricular pressure value and of an average of the detected or determined aortic pressure value, the detected or determined left ventricular pressure value is the peak of the detected or determined left ventricular pressure value ($LVP_{max}$), and the detected or determined aortic pressure value is the peak of the detected or determined aortic pressure value ($AOP_{max}$).

Once the coupling factor k is determined, the speed can be adjusted.

Figure 9:
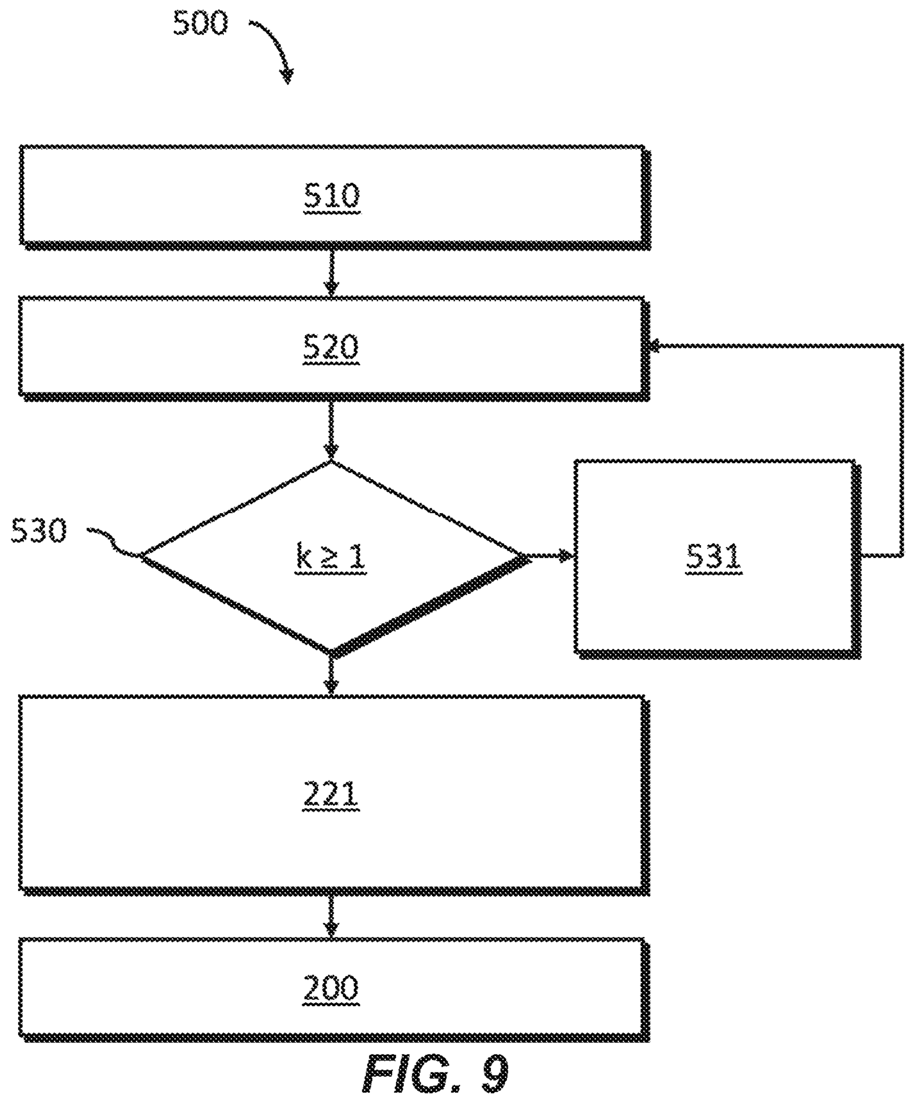
FIG. 9 is a flowchart of an embodiment of a startup routine used before the first selectable operating mode is utilized.

As shown in FIG. 9, when the coupling factor k≥1 (530), the rotational speed may be adjusted by a sixth amount, and then, after a fixed period of time, the coupling factor k may be determined again, and the speed may be adjusted again. In some embodiments, the fixed period of time may be between 5 and 30 seconds, such as between 10 seconds. In one embodiment, the sixth amount may be between 5% and 30% of a range of the rotational speed of the motor within which the processor is configured to perform the first selectable operating mode. As described above, in some embodiments, this range may be between 12,000 rpm and 20,000 rpm. For example, if the motor is designed to be controlled in this operating mode when rotating between, e.g., 31,000 rpm and 46,000 rpm, the operating speed range is 15,000 rpm, and thus, this sixth amount would be between 750 rpm and 4,500 rpm. In one embodiment, the sixth amount is between 2,000 rpm and 3,000 rpm.

However, once the coupling factor k<1, a different path may be followed. Specifically, if the coupling factor k is determined to be less than 1, the rotational speed of the motor may be adjusted in accordance with the first selectable operating mode 221 as described above. In one embodiment, and referring to FIG. 2, the speed is only adjusted if the coupling factor k is determined to be greater than a first threshold value ($T_1$) 230 or the coupling factor k is determined to be less than a second threshold value ($T_2$) 231. If the coupling factor k is between the first threshold value ($T_1$) and the second threshold value ($T_2$), the speed adjustment process is essentially ignored, and steps 210 and 220 are repeated.

Once the coupling factor k is determined to be greater than a first threshold value 230, a first subprocess 232 is entered into, whereby (as disclosed previously), the speed is increased until the coupling factor is less than a third threshold value ($T_3$). Specifically, in the first subroutine 232, if the coupling factor k is greater than a first threshold value ($T_1$) 234, then the rotational speed of the motor may be increased by a first amount 235; the rotational speed of the motor may be increased by a second amount 237 when the coupling factor k is less than or equal to the first threshold value ($T_1$) and greater than a third threshold value ($T_3$) 236. The second amount of motor speed increase (i.e., the absolute value of the change in motor speed caused by the second amount) may be smaller than the first amount (i.e., the absolute value of the change in motor speed caused by the first amount). After the speed adjustments (235, 237) are made, the pressures are measured, and the coupling factor k is determined again 238 as described previously for steps 220 and 221. This subprocess 232 may be repeated until the coupling factor k is less than or equal to the third threshold value ($T_3$), at which time the subprocess 232 ends and the process returns to measuring pressures in step 210.

Once the coupling factor k is determined to be less than a second threshold value 231, a second subprocess 233 may be entered into, whereby (as disclosed herein), the speed is decreased until the coupling factor is greater than a fourth threshold value ($T_4$), which may be the same as the third threshold value ($T_3$) in some embodiments. Specifically, in the second subroutine 233, if the coupling factor k is less than the fourth threshold value ($T_4$) and greater than or equal to the second threshold value ($T_2$) 244, the rotational speed of the motor may be decreased by a third amount 245; the rotational speed of the motor may be decreased by a fourth amount 243 when the coupling factor k is greater than or equal to a fifth threshold value ($T_5$) and less than the second threshold value ($T_2$) 242; and if the coupling factor k is less than the fifth threshold value ($T_5$) 239, the rotational speed of the motor may be decreased by a fifth amount 240. The fourth amount of motor speed decrease (i.e., the absolute value of the change in motor speed caused by the fourth amount) may be smaller than the decrease of fifth amount (i.e., the absolute value of the change in motor speed caused by the fifth amount). The third amount of motor speed decrease (i.e., the absolute value of the change in motor speed caused by the third amount) may be smaller than the fourth amount of motor speed decrease (i.e., the absolute value of the change in motor speed caused by the fourth amount). After the speed adjustments (240, 243, 245) are made, the pressures are measured, and the coupling factor k is determined again 241 as described previously for steps 220 and 221. This subprocess 233 is repeated until the coupling factor k is greater than or equal to the fourth threshold value ($T_4$), at which time the subprocess 233 ends and the process returns to measuring pressures in step 210.

As the fifth threshold value may be quite low, and often indicative of a potential concern, the processor 110 may be further configured to cause an alarm notification to be activated if the coupling factor k is determined to be less than the fifth threshold value. The alarm notification may remain until the coupling factor k is determined to be greater than or equal to another threshold value, this other threshold value being greater than the fifth threshold value and less than the fourth threshold value. In some embodiments, this other threshold value may be between 20% and 50% of a target coupling factor k value.

After a fixed period of time (e.g., the same fixed period of time as above, following step 531), the processor may then automatically begin to operate according to the first selectable method 200.

Figure 10:
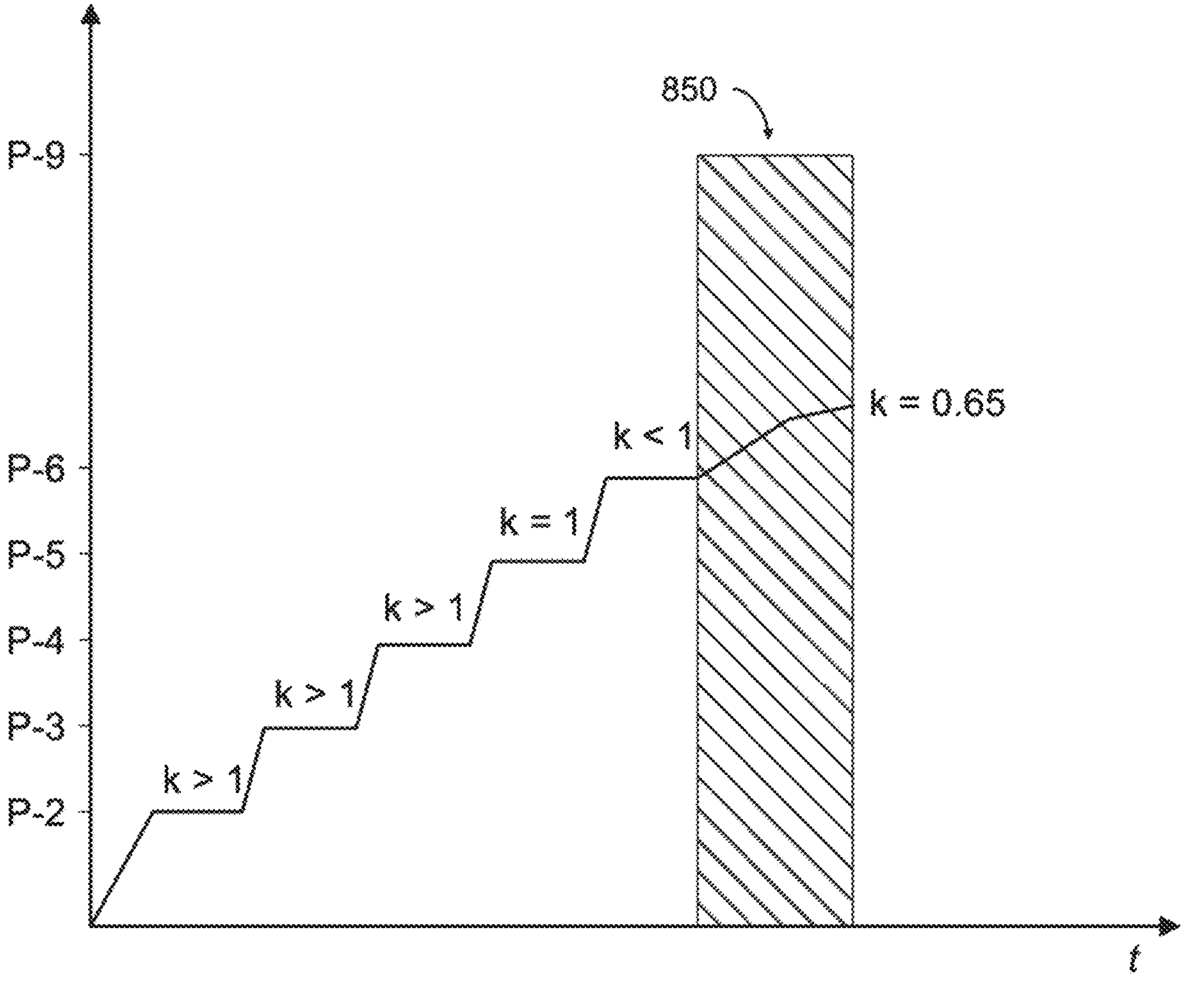
FIG. 10 is a graphical depiction of a startup routine for a catheter-based intravascular blood pump.

This startup process is illustrated in FIG. 10, where it can be seen that, starting from 0, the rotational speed may be first brought up to a minimum operating speed (here, P-2). After a period of time (here, 10 seconds), the coupling factor k may be determined to be greater than or equal to 1, so the speed is increased by a sixth amount to P-3. This process may be repeated several times until the speed reaches P-6, after which time the coupling factor k is then determined to be less than 1. In the period where the coupling factor k is less than 1 850, adjustments may be made according to the first selectable operating mode, shown in FIG. 10 as slowly adjusting the speed until the coupling factor k=0.65.

The controller 100 also may be configured to allow the motor to operate in other modes beyond the first selectable operating mode. That is, the controller 100 may be configured for use even if, e.g., the blood pump 50 is not operating in parallel with an ECMO device 90. In one embodiment, the controller 100 may be configured to operate in at least one other operating mode. For example, the controller 100 may be configured to operate in at least two other operating modes.

In one embodiment, the processor 110 may be further configured to operate in: (i) a second selectable operating mode where the processor 110 receives a selection of one of a plurality of predetermined operating rotational speeds and then adjusts the rotational speed of the motor to the selected predetermined operating rotational speed; and (ii) a third selectable operating mode where the processor 110 is configured to increase the rotational speed of the motor at a predetermined rate to a maximum operating rotational speed.

In some embodiments, the controller 100 may be configured to exit the first selectable operating mode 200 if the pressure values used to control the motor are determined to be unreliable. As will be appreciated, unreliability may be determined in any manner known to those of skill in the art, including, e.g., whether the determined pressures are within a predetermined range of expected pressures, or if the standard deviation of the measured pressures is above a threshold value.

In some embodiments, while operating using the first selectable operating mode 200, the processor may be further configured to determine if the detected or determined aortic pressure value, the detected or determined left ventricular pressure value, or both are unreliable, and when the detected or determined aortic pressure value, the detected or determined left ventricular pressure value, or both have been determined as unreliable for a period of time, switch from the first selectable operating mode to a second selectable operating mode. In some embodiments, the period of time here may be between 30 seconds and 5 minutes, such as 2 minutes. In some embodiments, the switch from the first mode to the second mode may comprise automatically determining which of a plurality of preset speeds is closest to, but not greater than, the current motor speed, and then adjusting the speed to that determined preset speed. In some embodiments, alarms or warnings may be generated when the signals are determined to be unreliable.

The disclosed blood pump system may generally comprise a controller 100 as described above and a catheter-based intravascular blood pump 50 that is operably connected to the controller.

The disclosed system (e.g., combining ECMO and VAD) may generally comprise two major groups of components. The first is an extra-corporeal membrane oxygenation (ECMO) system, such as a VA-ECMO system (e.g., ECMO device 90, flow controller 99, and the various associated tubes, fittings, etc.). The second is a blood pump system adapted to work in parallel with the ECMO system, the blood pump system comprising a controller 100 as described above and a catheter-based intravascular blood pump 50 that is operably connected to the controller.

Those skilled in the art will recognize or be able to ascertain using no more than routine experimentation many equivalents to the specific embodiments of the invention described herein. Such equivalents are intended to be encompassed by the following claims.

Embodiments of the present disclosure are described in detail with reference to the figures wherein like reference numerals identify similar or identical elements. It is to be understood that the disclosed embodiments are merely examples of the disclosure, which may be embodied in various forms. Well known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

What is claimed is:

1. A controller for a blood pump, in particular a catheter-based intravascular blood pump, the controller comprising:

a processor configured to control a rotational speed of a motor of the catheter-based intravascular blood pump using a first selectable operating mode, wherein the first selectable operating mode comprises the following steps:

detecting or determining aortic pressure values and left ventricular pressure values at a frequency of 0.5 Hz or greater;

determining a coupling factor k every 1 to 5 seconds using the detected or determined aortic pressure value and the detected or determined left ventricular pressure value; and causing at least one adjustment to the rotational speed of the motor based on the determined value of the coupling factor k, where increasing rotational speed increases the left ventricle unloading, and decreasing the rotational speed decreases the left ventricle unloading, the at least one adjustment being:

increasing the rotational speed of the motor by a first amount when the coupling factor k is greater than a first threshold value;

increasing the rotational speed of the motor by a second amount when the coupling factor k is less than or equal to the first threshold value and greater than a third threshold value, the second amount being smaller than the first amount;

decreasing the rotational speed of the motor by a third amount when the coupling factor k is greater than or equal to a fourth threshold value and less than a second threshold value;

decreasing the rotational speed of the motor by a fourth amount when the coupling factor k is greater than or equal to a fifth threshold value and less than the fourth threshold value, the fourth amount being larger than the third amount;

decreasing the rotational speed of the motor by a fifth amount when the coupling factor k is less than a fifth threshold value, the fifth amount being larger than the fourth amount; or a combination thereof.

2. The controller according to claim 1, wherein the coupling factor k is a quotient of an average of the detected or determined left ventricular pressure value and of an average of the detected or determined aortic pressure value.

3. The controller according to claim 2, wherein the average of the detected or determined left ventricular pressure value and the average of the detected or determined aortic pressure value is determined over a third predetermined time interval.

4. The controller according to claim 3, wherein the third predetermined time interval is between 8 and 12 seconds.

5. The controller according to claim 1, wherein the processor is further configured to operate in a second selectable operating mode where the processor receives a selection of one of a plurality of predetermined operating rotational speeds and adjusts the speed of the motor to the selected predetermined operating rotational speed; and the processor is further configured to operate in a third selectable operating mode where the processor is configured to increase the rotational speed of the motor at a predetermined rate to a maximum operating rotational speed.

6. The controller according to claim 5, wherein the processor is further configured to:

while operating using the first selectable operating mode, determine if the detected or determined aortic pressure value, the detected or determined left ventricular pressure value, or both are unreliable; and when the detected or determined aortic pressure value, the detected or determined left ventricular pressure value, or both have been determined as unreliable for a second period of time, switch from the first selectable operating mode to the second selectable operating mode.

7. The controller according to claim 6, wherein the second period of time is between 30 seconds and 5 minutes.

8. The controller according to claim 1, wherein the processor is configured to adjust the rotational speed of the motor in the first selectable operating mode in a first predetermined time interval.

9. The controller according to claim 8, wherein the first predetermined time interval is between 5 and 20 seconds.

10. The controller according to claim 1, wherein the second amount is 0.8-1.9% of an operating range of the rotational speed of the motor within which the processor is configured to perform the first selectable operating mode, the first amount and fourth amount are 2-4.5% of the operating range, and the third amount is 8-19% of the operating range.

11. The controller according to claim 10, wherein the operating range of the rotational speed of the motor is between 12,000 rpm and 22,000 rpm.

12. The controller according to claim 1, wherein the processor is further configured to detect suction events, and responding to such suction events by:

causing the rotational speed of the motor to decrease by a fifth amount if a first suction event is detected;

causing the rotational speed of the motor to decrease by a sixth amount if a second suction event is detected; and reducing an upper limit of the rotational speed of the motor by the sixth amount for a first period of time after the second suction event is detected within a predetermined window of time.

13. The controller according to claim 12, wherein the first period of time is between 10 minutes and 30 minutes, and the predetermined window of time is between 30 seconds and 5 minutes.

14. The controller according to claim 1, wherein the processor is further configured to, prior to performing the first selectable operating mode:

increase the rotational speed of the motor from zero to a minimum rotational speed the processor is configured to use when performing the first selectable operating mode;

determine the coupling factor k using a detected or determined aortic pressure value and a detected or determined left ventricular pressure value; and adjust the rotational speed of the motor based on the value of the coupling factor k, by:

if $k \geq 1$, increasing the rotational speed by a sixth amount, and after a fixed period of time, repeating steps b-c; and if $k<1$, adjusting the rotational speed of the motor according to the first selectable operating mode, and after the fixed period of time, control the rotational speed of the motor according to the first selectable operating mode.

15. The controller according to claim 14, wherein the sixth amount is between 5% and 30% of a range of the rotational speed of the motor within which the processor is configured to perform the first selectable operating mode.

16. The controller according to claim 1, wherein the processor is further configured to cause an alarm notification to be activated if the coupling factor k is determined to be less than the fifth threshold value until the coupling factor k is determined to be greater than or equal to a sixth threshold value, the sixth threshold value being greater than the fifth threshold value and less than the fourth threshold value.

17. The controller according to claim 16, wherein the sixth threshold value is between 20% and 50% of a target coupling factor k value.

18. The controller according to claim 1, wherein the processor is further configured to keeping the rotational speed of the motor constant when the coupling factor is equal to the second threshold value.

19. The controller according to claim 1, wherein the processor is configured to adjust the rotational speed of the motor based when the determined value of the coupling factor k is greater than the first threshold value or less than the second threshold value, by:

while the coupling factor k is greater than the third threshold value, repeating the steps of:

increasing the rotational speed of the motor by the first amount when the coupling factor k is greater than the first threshold value and increasing the rotational speed of the motor by the second amount when the coupling factor kis less than or equal to the first threshold value and greater than a third threshold value; and determining a coupling factor k using a detected or determined aortic pressure value and a detected or determined left ventricular pressure value; and while the coupling factor k is greater than the third threshold value, repeating the steps of:

decreasing the rotational speed of the motor by a third amount when the coupling factor k is greater than or equal to a fourth threshold value and less than a second threshold value, decreasing the rotational speed of the motor by a fourth amount when the coupling factor k is greater than or equal to a fifth threshold value and less than the fourth threshold value, the fourth amount being larger than the third amount, and decreasing the rotational speed of the motor by a fifth amount when the coupling factor k is less than a fifth threshold value, the fifth amount being larger than the fourth amount; and determining a coupling factor k using a detected or determined aortic pressure value and a detected or determined left ventricular pressure value.

20. The controller according to claim 1, wherein the first threshold value is 0.75, the second threshold value is 0.55, the third threshold value and the fourth threshold value are 0.55, and the fifth threshold value is 0.15.

21. The controller according to claim 1, wherein the first threshold value is a target coupling factor k value plus a defined value, the second threshold value is the target coupling factor k value minus the defined value, the third threshold value and the fourth threshold value are the target coupling factor k value, and the fifth threshold value is a value that is 15%-35% of the target coupling factor k value.

22. The controller according to claim 1, wherein the processor is further configured to:

detect whether an extra-corporeal membrane oxygenation (ECMO) device is operably connected to the controller, and prevent the selection or performance of the first selectable operating mode if the ECMO device is not detected;

receive a selection indicating the processor should operate the blood pump using the first selectable operating mode; or a combination thereof.

23. The controller according to claim 1, further comprising:

a display controlled by the processor;

a first port configured to operably connect the processor with the catheter-based intravascular blood pump;

a second port configured to operably connect the processor with an extra-corporeal membrane oxygenation (ECMO) system; and a housing configured to contain at least the processor.

24. A blood pump system, comprising:

a controller according to claim 1; and a catheter-based intravascular blood pump operably connected to the controller.

25. A system, comprising:

an extra-corporeal membrane oxygenation (ECMO) system; and a blood pump system adapted to work in parallel with the ECMO system, the blood pump system comprising a controller according to claim 1 and a catheter-based intravascular blood pump operably connected to the controller.

* * * * *